United States Patent [19]

Rolleston

[11] 4,454,107

[45] Jun. 12, 1984

[54] TC99M-PHENIDA, RADIOSCINTIGRAPHIC AGENT FOR DIAGNOSIS OF HEPATONILIARY DISEASE

[75] Inventor: Richard E. Rolleston, Dollard des Ormeaux, Canada

[73] Assignee: Merck & Co., Inc., Rahway, N.J.

[21] Appl. No.: 412,747

[22] Filed: Aug. 30, 1982

[51] Int. Cl.³ .................... A61K 43/00; A61K 49/00
[52] U.S. Cl. ........................ 424/1.1; 260/429 R; 422/61; 564/50; 564/53; 564/59; 564/195; 548/163; 548/180
[58] Field of Search ............. 424/1.1; 260/429 R; 564/49, 50, 53, 58, 59, 195; 422/61; 548/163, 180

[56] References Cited

U.S. PATENT DOCUMENTS

| 4,017,596 | 4/1977 | Loberg et al. ................ 424/1 |
| 4,316,883 | 2/1982 | De Schrijver et al. ........ 424/1.1 |
| 4,318,898 | 3/1982 | Molter et al. ................ 424/1.1 |
| 4,350,674 | 9/1982 | Molter et al. ................ 424/1.1 |

FOREIGN PATENT DOCUMENTS

| 1308793 | 7/1970 | United Kingdom ............ 424/1 |
| 1545427 | 5/1977 | United Kingdom ............ 424/1 |
| 2090252 | 7/1982 | United Kingdom ............ 424/1.1 |

OTHER PUBLICATIONS

Graham et al., J. Pharm. Sci., 71 (3); 362-364 (1982).
Azuma, J. Nucl. Med., 23 (6); 517-524 (1982).
"Radiopharmaceuticals"II, pp. 587, 592.
"Journal of Nuclear Medicine" 17, pp. 633-638 (1976).
"Journal of Nuclear Medicine" 18, pp. 455, 624, 997 (1977).
"Radiology" 128, p. 793 (1978).
"European Journal of Nuclear Medicine" 4, p. 445 (1979).
"Journal of Pharmaceutical Sciences" 68, p. 317 (1979).
"Journal of Pharmaceutical Sciences" 69, p. 731 (1980).

Primary Examiner—Christine M. Nucker
Attorney, Agent, or Firm—Thomas E. Arther; Daniel T. Szura; Hesna J. Pfeiffer

[57] ABSTRACT

This invention relates to novel derivatives of imino diacetic acid of the formula:

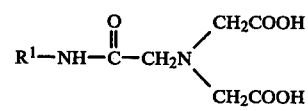

wherein $R^1$ is selected from the group consisting of:

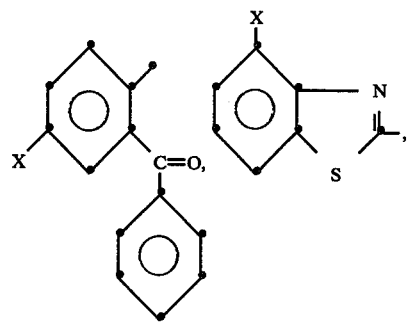

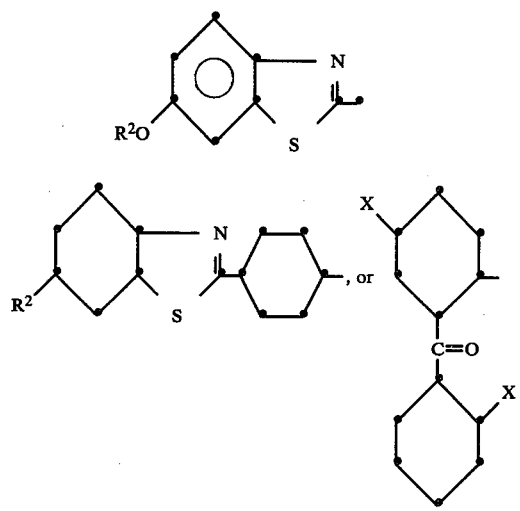

wherein X is halo (chloro, bromo or iodo) and $R^2$ is lower alkyl of from 1-5 carbon atoms. It also relates to a novel diagnostic kit for hepatobiliary imaging comprising ingredients employed in the intravenous injection of a complex of technetium 99m, and an imino diacetic acid of the above formula. It also relates to a process for preparing said compounds by reaction of nitrilotriacetic acid anhydride and an amine of the formula $R^1NH_2$ wherein $R^1$ is as defined hereinabove.

12 Claims, No Drawings

TC99M-PHENIDA, RADIOSCINTIGRAPHIC AGENT FOR DIAGNOSIS OF HEPATONILIARY DISEASE

BACKGROUND OF THE INVENTION

In radiopharmacy, technetium 99m is obtained as an aqueous solution of sodium pertechnetate, where Tc has the oxidation state +VII. Several reducing agents have been employed to reduce the pertechnetate to a lower oxidation state. The stannous ion in the form of a water soluble salt is the most commonly used agent, particularly as the stannous chloride.

In the reduced form, Tc forms cations which are complexed with a number of complexing agents, such as diethylene triamine pentacetic acid, methylenediphosphonic acid, and imino diacetic acids. The Tc II to Tc V cations are hydrated oxo ions, and in this oxidation state ions are generally referred to in the radiopharmaceutical literature as "reduced pertechnetate-Tc99m".

The use of substituted iminodiacetic acids and substituted imino diacetic acids complexed with a form of technetium 99m and stannous ion are disclosed to be useful as agents for imaging the hepatobiliary system by Loberg et al. in U.S. Pat. No. 4,017,596. Other related compounds are reported by Subramanian J. Nucl. Med. 18, 624 (1977). These compounds are substituted nitrilotriacetic acid mono amides. Other substituted iminodiacetic acids are disclosed in U.K. Patent specification No. 1,545,437 as useful in diagnosing hepatobiliary function using complexes with technetium 99m; in U.K. patent specification No. 1,308,793 as useful chelating agents. Other iminodiacetic acids useful as chelating agents with technetium 99m are disclosed as follows:

| | | |
|---|---|---|
| 1. Radiopharmaceuticals II | p 587, 592 | |
| 2. Journal of Nuclear Medicine | 17, 633–8 | (1976) |
| 3. Journal of Nuclear Medicine | 18, 624 | (1977) |
| 4. Journal of Nuclear Medicine | 18, 455 | (1977) |
| 5. Journal of Nuclear Medicine | 18, 997 | (1977) |
| 6. Radiology | 128, 793 | (1978) |
| 7. European Journal of Nuclear Medicine | 4, 445 | (1979) |
| 8. Journal of Pharmaceutical Sciences | 68, 317 | (1979) |
| 9. Journal of Pharmaceutical Sciences | 69, 731 | (1980) |

It is known from these publications that chelates of certain of the above noted substituted iminodiacetic acids with technetium 99m are excreted through both the urine and the biliary ducts. One of the drawbacks of using these prior art compounds in visualizing the hepatobiliary system is that in the case of liver disease the visualization of the hepatobiliary system is unsatisfactory. This is believed to be true because of improper functioning of the biliary ducts in which case excretion of the compounds is accomodated by way of the urine.

Substituted iminodiacetic acids, as defined hereinabove, are capable of forming molecular complexes with technetium 99m in the reduced form. These radiolabelled biological agents have a high degree of in vivo stability and are highly selective for the hepatobiliary system.

It is an object of the invention to provide such complexes useful in diagnosing hepatobiliary function in the presence of liver disease. It is a further object of the invention to provide a novel diagnostic kit for hepatobiliary imaging comprising a freeze-dried mixture of a soluble stannous salt and a novel iminodiacetic acid of the formula given above. A still further object of the present invention is to provide a process for the preparation of said compounds by reaction of nitrilotriacetic acid anhydride and an amine of the formula $R^1NH_2$ wherein $R^1$ is as defined above.

SUMMARY OF THE INVENTION

The above objects are achieved by providing a radiolabelled diagnostic agent which combines the high target organ specificity of the substituted iminodiacetic acids mentioned hereinabove with the combined ability, even in the presence of liver disease, to accumulate in the hepatobiliary system even in systems in which the common bile duct is partially blocked, as for example by ligation of the duct in laboratory animals.

The invention is based on the discovery that the substituted iminodiacetic acids defined hereinabove and technetium 99m in the reduced state form complexes which are highly specific to the hepatobiliary system and have excellent imaging properties even in the presence of liver disease.

In accordance with the subject invention there are provided substituted iminodiacetic acids of the formula:

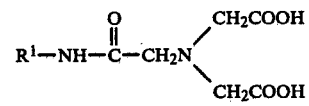

wherein $R^1$ is selected from the group consisting of:

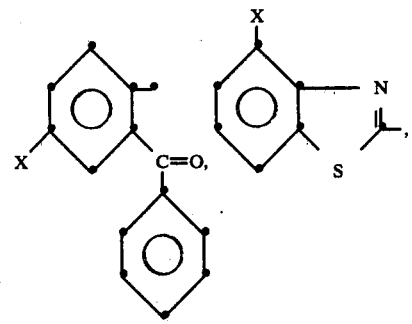

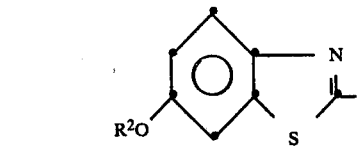

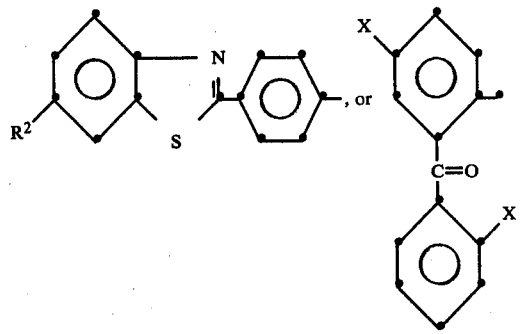

wherein x is halo (chloro bromo or iodo) and $R^2$ is lower alkyl of from 1–5 carbon atoms preferably methyl. Another aspect of the present invention is the provision of a process for the preparation of said substituted iminodiacetic acids. In accordance with the process of preparing said substituted iminodiacetic acids, nitrilotriacetic acid anhydride is contacted in solution with a substituted amine in accordance with the following structural equation:

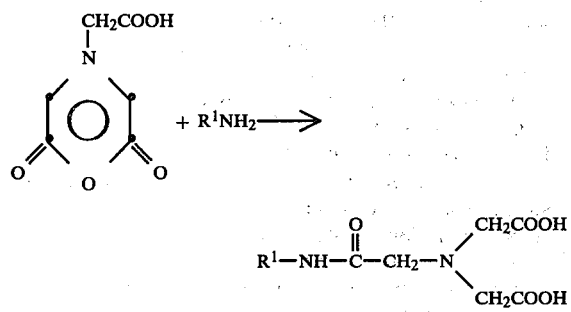

wherein $R^1$ is defined as hereinabove. The process is carried out by contacting the two reactants, preferably in a solvent for the reactants. The solvent selected should be relatively inert under the reaction conditions and aromatic hydrocarbons especially toluene are preferred. The reaction mixture is heated to 40°–100° for a period of 30 minutes to about 6 hours, preferably to 90°–100° for approximately 1 hour. Following the reaction, the solvent is removed by evaporation and the residue containing the desired product is slurried with dilute aqueous alkali, filtered and the filtrate containing the product is washed with a solvent such as chloroform and ether and purified by treatment with charcoal and precipitated by treatment with acid. Further purification of the product is accomplished by recrystallization from a solvent for the product. It also relates to a novel diagnostic kit for heptaobiliary imaging comprising ingredients employed in the intravenous injection of a complex of technetium 99m, stannous ion, and an iminodiacetic acid of the above formula. It also relates to a process for preparing said compounds by reaction of nitrilotriacetic acid anhydride and an amine of the formula $R^1NH_2$.

It also relates to a method of imaging the hepatobiliary system of a patient (human or domestic animal) which comprises the intravenous administration of a molecular complex of technetium 99m, stannous ion and a substituted iminodiacetic acid as defined hereinabove and visualizing the hepatobiliary system by use of an imaging device such as a gamma camera to record the areas in which the radioactive molecular complex accumulates for diagnostic purposes.

The complexes of applicant's compounds with technetium 99m and stannous chloride are readily prepared from freeze-dried mixtures of the specified iminodiacetic acid and stannous chloride by reaction with a solution of technetium 99m in the form of the pertechnetate.

In accordance with the present invention, there is provided a diagnostic kit suitable for use in scintigraphic studies of the hepatobiliary system. The kit ordinarily contains sufficient material for more than one dose. It comprises a freeze-dried mixture of the components suitable for reconstitution with a solution of sodium pertechnetate. The present kit employs individual vials each containing a reducing agent and the substituted iminodiacetic acid for use in the preparation of an injectable hepatobiliary imaging agent. One such kit comprises a freeze-dried mixture of a water soluble stannous salt and the preferred compound N-[N'-(2-benzoyl-4-chlorophenyl)carbamoylmethyl]iminodiacetic acid (PHENIDA).

In the process of preparing the instant diagnostic kit it is essential that a single vial be prepared observing aseptic techniques and using normal saline solution as a diluent so that the ingredients when reconstituted with technetium 99m in the reduced form are compatible with body fluid and may be intravenously injected without further treatment after mixing. Another important feature of the present invention is the ratio of the amounts of the substituted iminodiacetic acid and the stannous salt employed as the reducing agent. Usually the ratio of substituted iminodiacetic acid to reducing agent is from 10–100 parts by weight of substituted iminodiacetic acid to 1 part by weight of reducing agent. It is important to the present invention that the weight ratio of PHENIDA to stannous salt is about 60:1. In preparing the components of the present kit the first component is prepared by dissolving 60 parts by weight of PHENIDA or the equivalent amount of a soluble salt and one part by weight of stannous chloride dihydrate in water made slightly acid with hydrochloric acid and adjusting to pH 4–8. The solution is diluted with water to a concentration of approximately 30 mg/ml of PHENIDA by weight and subdividing the bulk solution into individual dosage amounts and aseptically freeze-dried to provide a readily soluble mixture of 60 mg PHENIDA and 1 mg stannous chloride as the dihydrate at pH 4–8.

The kit comprising the freeze-dried mixture of PHENIDA and stannous chloride is readily employed as a diagnostic tool for hepatobiliary imaging in the following manner. To the freeze-dried mixture of PHENIDA and stannous chloride is added a solution of 2–8 ml of a solution containing approximately 10–200 millicures of sodium pertechnetate Tc99m. The resulting injectable solution of PHENIDA-stannous complex labelled with Tc99m can be used immediately without further treatment.

In utilizing the instant kit for hepatobiliary imaging, an aqueous solution of from 2–8 ml of the required amount of sodium pertechnetate Tc99m (available as instant technetium 99m or from a sterile generator of the type described in U.S. Pat. No. 3,369,121) is mixed with a freeze-dried mixture of PHENIDA and stannous chloride to form a solution of reduced pertechnetate ion bound to the PHENIDA compound which solution is ready for injection after standing for 15 minutes to ensure maximum binding. Intravenous injection of approximately 10 millicures of the Tc99m PHENIDA-stannous complex is followed by serial imaging of the hepatobiliary system and gut starting at 30 minutes. The present improved kit is highly satisfactory because of its simplicity and because of the advantage that it may be readily employed to image the hepatobiliary system in patients suffering from liver disease, as for instance, liver disease indicated by elevated serum bilirubin levels.

EXAMPLE 1

Preparation of PHENIDA

Step 1

Preparation of 2,6-diketo-N-carboxymethyl morpholine (NTA anhydride)

A round bottom flask is charged with dimethylformamide 72 g, acetic anhydride 25 g, pyridine 2 g, and nitrilotriacetic acid 38.2 g and the suspension is nitrogen purged for several minutes. The flask is stoppered and the mixture is stirred at room temperature for 3 days. A small amount of unreacted NTA is filtered out. The bulk of the solvent 79 ml is removed in vacuo at a bath temperature of 60°–70° C. The resulting viscous solution is twice roto-vacued after two successive additions of 40 ml dimethylformamide.

Step 2

Preparation of N-[N'-(2-benzoyl-4-chlorophenyl)carbamoylmethyl]iminodiacetic acid PHENIDA To the viscous solution of NTA anhydride is added 300 ml toluene. The mixture is stirred at room temperature until uniform. Then 46.3 gm of 2-amino-5-chlorobenzophenone dissolved in 300 ml toluene is added to the stirred solution of NTA anhydride and heated at 90°–100° C. for 1 hour. After cooling, the reaction mixture is flashed to dryness. The residue is taken up in 400 ml of 1N sodium hydroxide and filtered. The filtrate is extracted with chloroform, ether and charcoaled. The charcoal is removed by filtration. The product is precipitated from the filtrate by the careful addition of 6N HCl. The precipitate is removed by filtration and recrystallized from hot methanol/water. M.P. 180°–186° C. (decomposition).

| NMR in DMSO-$d_6$ with TMS | |
| --- | --- |
| $\delta = 3.23$ singlet | N—CH$_2$C(=O)—N |
| $\delta = 3.33$ singlet | —N—(CH$_2$—C(=O)(O−))$_2$ |
| $\delta = 7.92$ doublet | aromatic protons |
| $\delta = 7.52$ multiplet | |
| $\delta = 10.3$ variable broad singlet | H–N– |

The procedure of Step 2 is repeated using an equivalent amount of the indicated amine reactant in place of the 2-amino-5-chlorobenzophenone with production of the products shown in the following table:

| Amine Reactant | Product | M.P. °C. |
| --- | --- | --- |
| 2-amino-4-chloro-benzothiazole | N—[N'—(4-chloro-benzothiazol-2-yl)carbamoylmethyl]iminodiacetic acid (A) | 210–13° dec |
| 2-amino-6-ethoxy benzothiazole | N—[N'—(6-ethoxybenzo-thiazol-2-yl)carbamoyl-methyl]iminodiacetic acid (B) | 223–26° dec |
| 2-(4-amino-phenyl)-6-methyl-benzo-thiazole | N—[N'—{4-(6-methyl-benzothiazol-2-yl)phenyl}carbamoylmethyl]imino diacetic acid (C) | 245–50° dec. |
| 2-amino-2',5 dichlorobenzo-phenone | N—[N'—{2-(2-chlorobenzoyl)-4-chlorophenyl}carbamoyl-methyl]iminodiacetic acid (D) | 185–88° dec. |

EXAMPLE 2

Preparation of kit containing a freeze-dried mixture of 60 mg of PHENIDA and 1 mg stannous chloride dihydrate per vial A solution is prepared by dissolving 6000 mg of PHENIDA in 100 ml 0.2N sodium hydroxide and adding 100 mg stannous chloride dihydrate dissolved in 10 ml acidulated water. The pH of the solution is adjusted to 5.5 using dilute hydrochloric acid and/or dilute aqueous sodium hydroxide solution. Finally the solution volume is adjusted to 200 ml using sterile distilled water and aseptically filtered using a sterilizing membrane.

The solution is sub-divided into two ml portions and filled into 10 ml vials. The sub-divided solutions are then aseptically freeze-dried to provide a readily soluble freeze-dried mixture of 60 mg PHENIDA and 1 mg stannous chloride dihydrate in each vial and stored in a nitrogen atmosphere. The procedure of this Example is repeated for each of the products A, B, C and D to prepare freeze-dried mixtures of stannous chloride and each of product A, B, C and D.

EXAMPLE 3

Use of Kit in Preparing Diagnostic Liver and Bile Duct Imaging Solution

Approximately 2–8 ml of the sterile saline solution of from 20–200 millicures of sodium pertechnate Tc99m is aseptically added to the contents of one of the vials described in the previous example. The volume is adjusted to 10 ml with sterile saline solution if desired. The resulting mixture is then shaken to provide the final dosage for Tc99m-PHENIDA-stannous complex suitable as an agent for imaging human or animal hepatobiliary systems. This final form usually contains more than enough for one intravenous dose, ordinarily 3–5 doses containing approximately 10 millicures per dose.

The above procedure is repeated using a freeze-dried mixture of stannous chloride and product A, B, C or D prepared in accordance with Example 2.

What is claimed is:

1. An imino-diacetic acid compound of the formula:

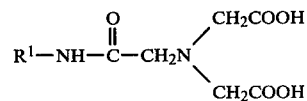

wherein $R^1$ is selected from the group consisting of:

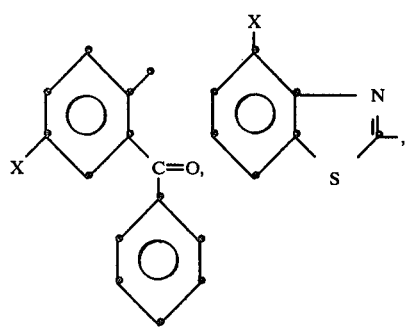

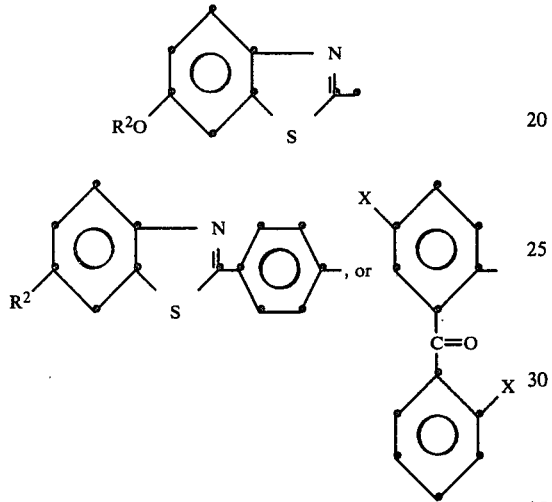

wherein X is halo and R² is loweralkyl of from 1–5 carbon atoms.

2. A compound of claim 1 which is N-[N'-(4-chlorobenzothiazol-2-yl)carbamoylmethyl]iminodiacetic acid.

3. A compound of claim 1 which is N-[N'-(6-ethoxybenzothiazol-2-yl)carbamoylmethyl]iminodiacetic acid.

4. A compound of claim 1 which is N-[N'-{4-(6-methylbenzothiazol-2-yl)phenyl}carbamoylmethyl]iminodiacetic acid.

5. A compound of claim 1 which is N-[N'-{2-(2-chlorobenzoyl-4-chlorophenyl}carbamoylmethyl]iminodiacetic acid.

6. A compound according to claim 1 of the formula

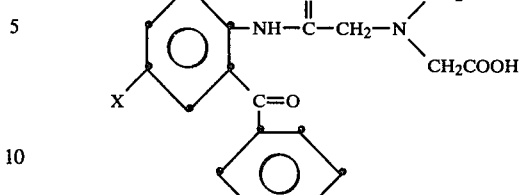

wherein X is halogen.

7. A compound according to claim 6 of the formula

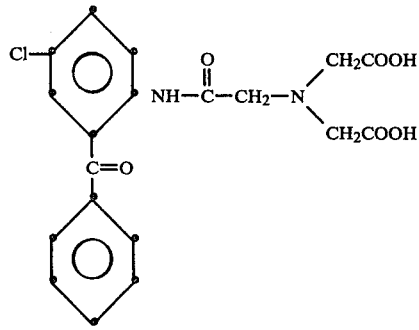

8. A molecular complex comprising a mixture of technetium 99m, a compound of claim 1 and a water soluble stannous salt.

9. A diagnostic kit for the preparation of an injectable solution incorporating technetium 99m which comprises a container of a lyophilized mixture of a compound of claim 1 and a water soluble tin salt.

10. A diagnostic kit for the preparation of an injectable solution incorporating technetium 99m which comprises a container of a freeze-dried mixture of the compound of claim 1 and stannous chloride.

11. A diagnostic kit according to claim 9 in which the weight ratio of the components is from 10–100 parts by weight of N-[N'-(2-benzoyl-4-chlorophenyl)carbamoylmethyl]iminodiacetic acid and 1 part of tin as stannous chloride dihydrate.

12. A method for imaging the hepatobiliary system which comprises the intravenous administration of a sterile solution of a molecular complex of claim 8.